(12) United States Patent
Van Gogh et al.

(10) Patent No.: US 8,043,227 B2
(45) Date of Patent: Oct. 25, 2011

(54) NON-INVASIVE SYSTEM AND METHOD FOR MEASURING SKIN HYDRATION OF A SUBJECT

(75) Inventors: Antonius Theodorus Marinus Van Gogh, Eindhoven (NL); Maarten Marinus Johannes Wilhelm Van Herpen, Eindhoven (NL)

(73) Assignee: Konklijke Philips Electronics N.V., Eindhoven (NL)

( * ) Notice: Subject to any disclaimer, the term of this patent is extended or adjusted under 35 U.S.C. 154(b) by 459 days.

(21) Appl. No.: 12/158,714

(22) PCT Filed: Dec. 26, 2006

(86) PCT No.: PCT/IB2006/055034
§ 371 (c)(1),
(2), (4) Date: Jun. 23, 2008

(87) PCT Pub. No.: WO2007/074422
PCT Pub. Date: Jul. 5, 2007

(65) Prior Publication Data
US 2008/0275319 A1   Nov. 6, 2008

(30) Foreign Application Priority Data
Dec. 28, 2005  (EP) .................................. 05301117

(51) Int. Cl.
*A61B 5/00* (2006.01)
(52) U.S. Cl. ........ 600/555; 600/306; 600/316; 600/346; 600/347
(58) Field of Classification Search .................. 600/555, 600/306–309, 316, 346–348, 365–366
See application file for complete search history.

(56) References Cited

U.S. PATENT DOCUMENTS

| | | | |
|---|---|---|---|
| 5,890,489 A | 4/1999 | Elden | |
| 6,241,663 B1 * | 6/2001 | Wu et al. | 600/310 |
| 6,488,677 B1 * | 12/2002 | Bowman et al. | 606/28 |
| 6,954,662 B2 * | 10/2005 | Freger et al. | 600/316 |

(Continued)

FOREIGN PATENT DOCUMENTS
WO   0210725 A2   2/2002
(Continued)

OTHER PUBLICATIONS

A. Dittmar, et al: Non Invasive Characterization of Skin Using Micro Thermal Diffusion Sensor, Engineering in Medicine and Biology Society, 1995. IEEE 17th Annual Conference, vol. 2, Sep. 20, 1995, Sep. 23, 1995, pp. 1569-1570.

(Continued)

*Primary Examiner* — Nicholas D Lucchesi
*Assistant Examiner* — Melissa A Snyder

(57) ABSTRACT

A non-invasive system and method for measuring skin hydration of a subject includes a thermistor used in transient mode to obtain a measurement of the thermal conductivity of the skin of the subject and a processor for determining a skin hydration value from the thermal conductivity measurement. The system for measuring skin hydration further includes a non-invasive system for detecting blood analyte concentration, such as glucose, with a spectroscopic device having e.g., an infrared source which generates infrared beam and detector for detecting transmitted radiation through portion (e.g., finger) of a subject. The system may also include skin hydrator which moisturizes the skin and is connected in a control loop to the system for measuring skin hydration. The system for detecting blood analyte concentration may include a photoacoustic device or a metabolic heat conformation device.

12 Claims, 3 Drawing Sheets

U.S. PATENT DOCUMENTS

Figure 1:
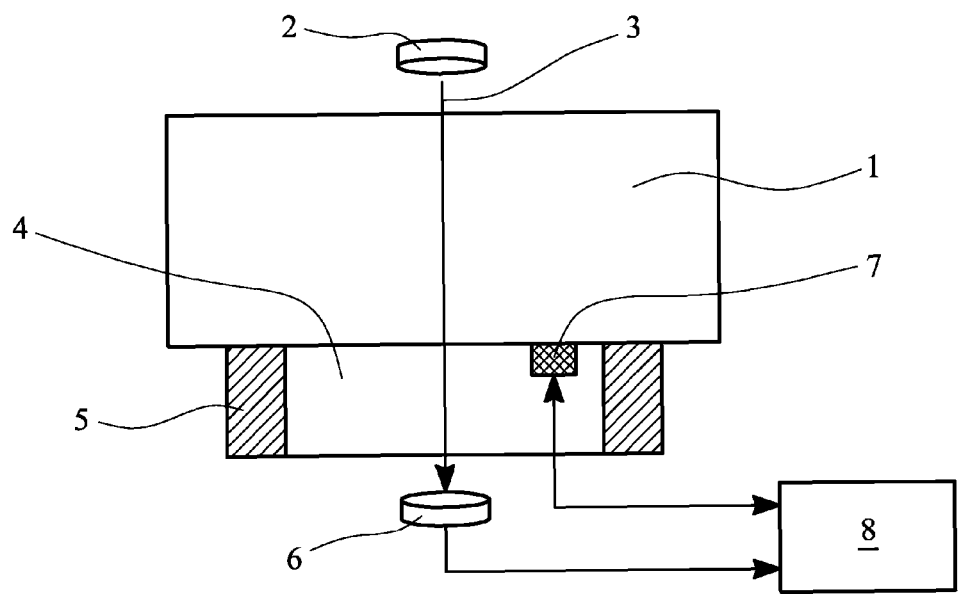

| | | | |
|---|---|---|---|
| 7,133,710 B2 * | 11/2006 | Acosta et al. | 600/316 |
| 2003/0023148 A1 | 1/2003 | Lorenz et al. | |
| 2004/0068163 A1 | 4/2004 | Ruchti et al. | |

FOREIGN PATENT DOCUMENTS

| | | | |
|---|---|---|---|
| WO | 02091947 A2 | 11/2002 | |
| WO | 03045235 A1 | 6/2003 | |
| WO | 03105664 A2 | 12/2003 | |
| WO | 2004042382 A1 | 5/2004 | |

OTHER PUBLICATIONS

Peng Xiao et al: Calibration of Optothermal Stratum Corneum Hydration Measurements, Review of Scientific Instruments, vol. 74. No. I, Jan. 2003, pp. 729-731.

O. K. Cho, et al: "Noninvasive Measurement of Glucose by Metabolic Heat Conformation Method"; Clinical Chemistry 50:10, 2004, pp. 1894-1898.

\* cited by examiner

NON-INVASIVE SYSTEM AND METHOD FOR MEASURING SKIN HYDRATION OF A SUBJECT

The present invention relates to a non-invasive system for measuring skin hydration of a subject. The term skin is used to refer to skin and exterior mucosa.

In a particularly advantageous embodiment of the present invention the system is comprised in an apparatus for detecting blood analyte concentration. The skin hydration value can be used to postpone the measurement of the blood analyte concentration until the skin hydration reaches a certain predetermined value or the skin hydration value can be used to correct for hydration during determination and calculation of the blood analyte concentration.

Currently the determination of the concentration of most blood constituents or analytes, for example glucose or cholesterol, is done invasively requiring a blood sample to be taken. The blood sample is taken and transferred to a laboratory or handheld device where it is analysed. Non-invasive analysis of blood constituents has many advantages over invasive techniques, e.g reduction in discomfort and infection risk for the subject.

However non-invasive analysis techniques must be both sensitive and specific for the particular analyte. When applied to a human subject the enormous complexity of the organism can result in interference of the analyte signal by other substances and also by other variables which can vary over time or from person to person.

A non-invasive measurement system is required to measure an analyte concentration through the skin of the subject. The physical state of the skin e.g. colour, roughness, hydration varies significantly between individuals and these skin variations are an important error source for many non-invasive analyte concentration measuring techniques.

Skin hydration varies between individuals and varies, sometimes rapidly in time, for a single individual e.g when the individual is sweating or the air humidity changes. Many non-invasive glucose measuring techniques in particular are based on absorption and/or scattering of infrared light. In the infrared part of the electromagnetic spectrum photon absorption of water varies significantly and is in general very high. Therefore a small change in water content of the outer skin layers has a major effect on the indicative signal of infrared based techniques. This is for two reasons, first that the intensity of the incoming excitation beam is affected by hydration levels as the beam has to travel through the skin before it can excite the relevant molecules e.g. glucose. Second because the scattered photons have to travel through the skin on their way back to the detector.

US 2004/0068163 discloses a method and apparatus for non-invasive determination of blood analytes, such as glucose, through near infrared spectroscopy. Physiological changes such as changes in water distribution among tissue compartments result in changes in optical properties of the tissue, which are detected. The detected changes are used for determining conditions not conducive to non-invasive measurement of glucose through near-infrared spectroscopy and for correcting the glucose measurements or measuring the glucose indirectly on the basis of the detected changes.

An object of the present invention is to provide a simple and cost-effective means of determining hydration of skin.

A further object of the invention is to improve the accuracy of non-invasive analyte concentration measurement.

The present invention relates to a non-invasive system for measuring skin hydration of a subject comprising;

a thermal conductivity measuring apparatus for obtaining a measurement of the thermal conductivity of the skin of the subject and a processor for determining a skin hydration value from the thermal conductivity measurement.

In living tissue the effective thermal conductivity is determined by conduction and convection. Conduction depends on the nature of the tissue and in particular the water content because proteins and lipids have the same thermal conductivity, which is approximately three times lower than that of water. Conduction is thus to a large extent determined by the water content. Convection in living tissue is caused by blood flow, mainly in the smallest vessels of the vascular system.

During the first two seconds of the determination of the thermal conductivity of a live subject by the sensor the heat flow is nearly fully determined by conduction i.e. the water content. From the $2^{nd}$ to the $6^{th}$ second the heat flow is determined both by conduction (water content) and convection (blood flow). Both the convective and conductive contribution can thus be determined.

Preferably the thermal conductivity measuring apparatus comprises;

a thermistor in thermal connection with the skin of the subject in use and a current supply for supplying current to the thermistor sufficient to maintain the resistance or temperature of the thermistor at a predetermined level, wherein the thermal conductivity measuring apparatus obtains a measurement of the thermal conductivity in dependence upon the current supplied to the thermistor.

Thermistors have the advantage that they are widely used, relatively inexpensive, can be very small and have a large dynamic range. A thermistor in transient mode can be used to measure the effective thermal conductivity of a portion of a subject in thermal contact with it. Transient mode refers to at least one measurement period consisting of a heating and cooling period. During the heating period a current is sent through the thermistor at a rate sufficient to maintain the temperature and resistance of the thermistor at a constant value. The heat dissipated by the thermistor equals the heat flow into the subject. The amount of dissipated heat is a measure for the thermal conductivity of the subject and the current supplied to the thermistor is thus a measure for the thermal conductivity of the object, i.e. when the thermal conductivity is high more power is required to keep the thermistor at an elevated temperature than when the thermal conductivity is low.

Preferably the system is comprised in a non-invasive apparatus for detecting blood analyte concentration. Skin hydration can be monitored until an optimum level for accurately detecting the analyte concentration is reached or the skin hydration value can be used to compensate the detected analyte concentration.

Preferably the system comprises a skin hydrating means so the skin hydration can be increased e.g. to a more favourable value for determining analyte concentration. More preferably the non-invasive system for measuring skin hydration is connected in a control loop to the skin hydrating means so the skin hydration is maintainable at a predetermined level. The system thus enables active control of the skin hydration to keep the skin hydration at a particular predetermined level thereby eliminating variations in hydration levels.

The present invention also relates to a method for measuring skin hydration comprising the steps of:

non-invasively measuring the thermal conductivity of the skin;

determining the hydration level of the skin from the thermal conductivity.

These and other aspects of the present invention will be apparent from and elucidated with reference to the embodiments described herein.

Figure 2:
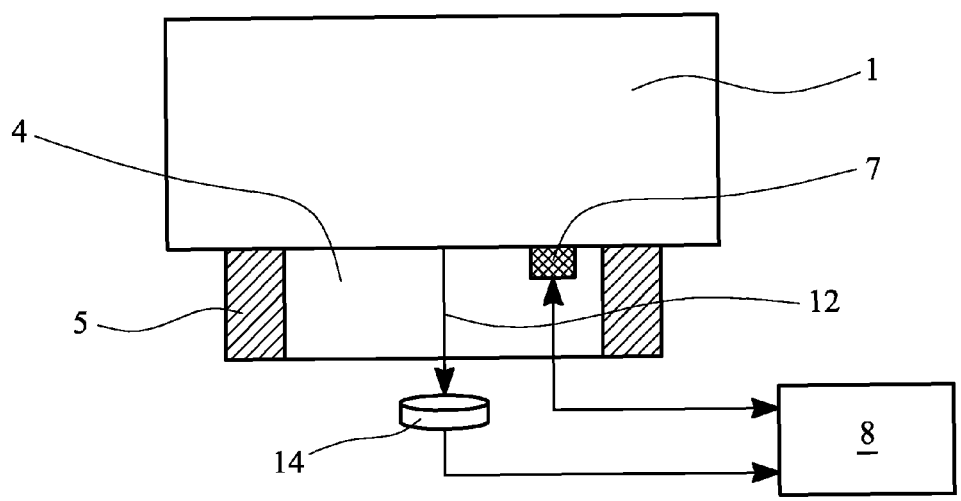
Figure 3:
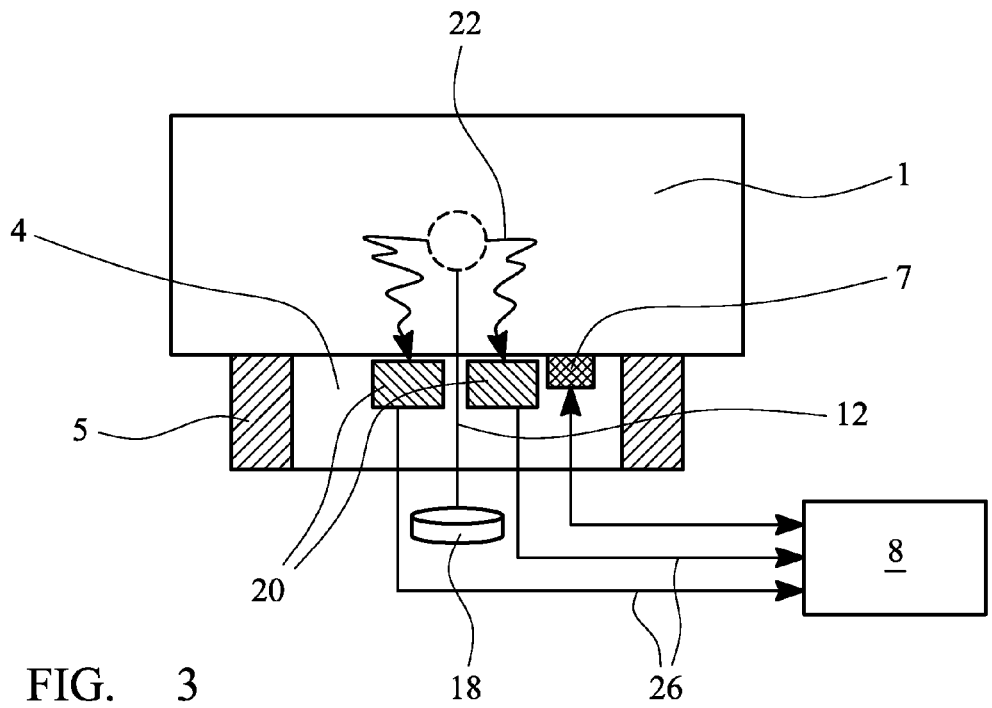
Figure 4:
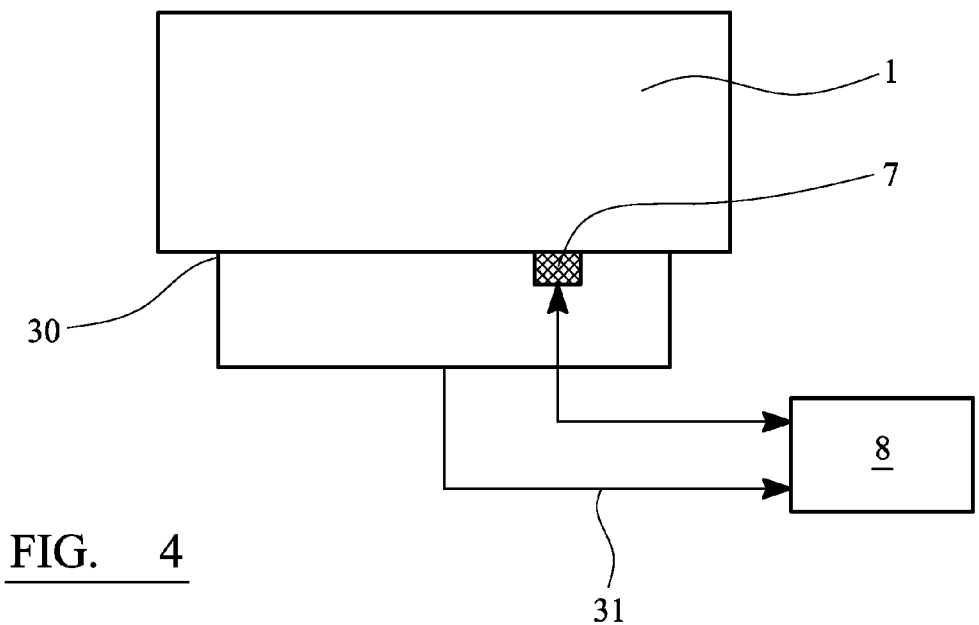
Figure 5:
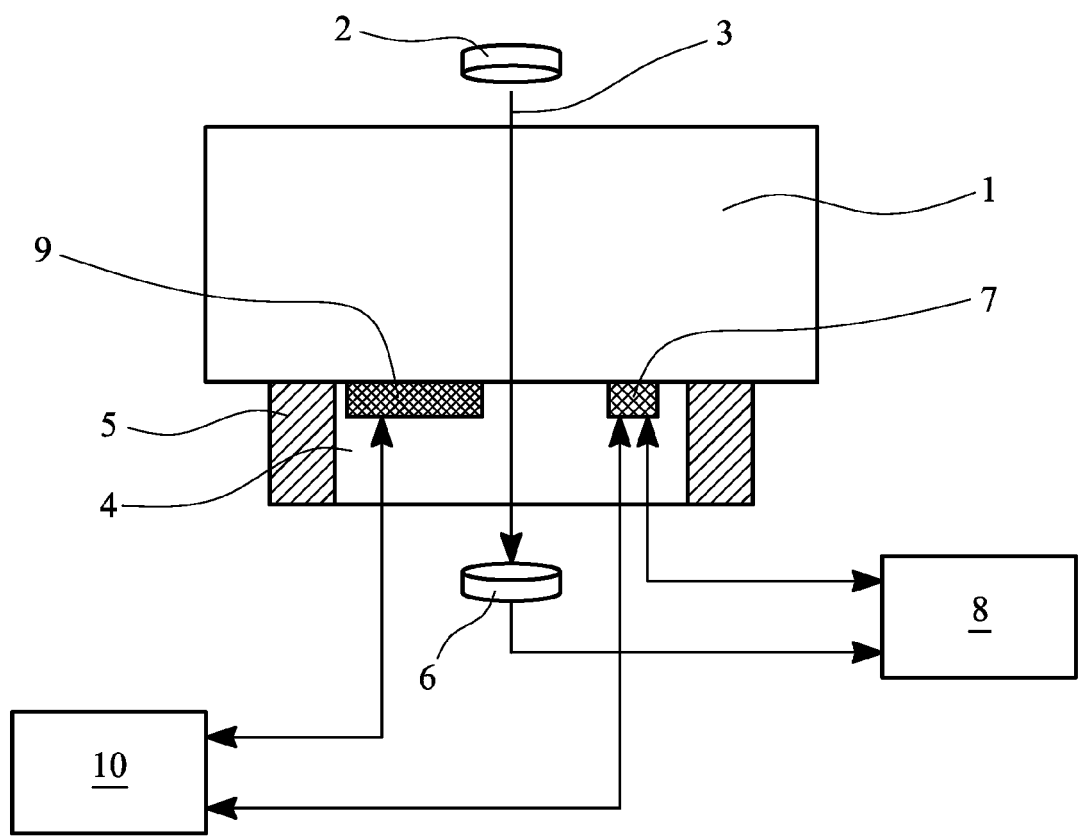

Embodiments of the present invention will now be described by way of examples only and with reference to the accompanying schematic drawings in which:

FIG. 1 shows a first embodiment of the invention;
FIG. 2 shows a second embodiment of the invention;
FIG. 3 shows a third embodiment of the invention;
FIG. 4 shows a fourth embodiment of the invention;
FIG. 5 shows a fifth embodiment of the invention.

The system illustrated in FIG. 1 may be used for measuring glucose concentration in particular and comprises an infrared source 2, which generates infrared beam 3, and an infrared detector 6 for detecting transmitted radiation. The system also comprises a window housing 5, window 4 and thermistor 7 embedded in the window 4. The signal generated by detector 6 is indicative of glucose concentration and is transmitted to processor 8 which determines the glucose concentration therefrom.

The system is applied to subject portion 1 (e.g. upper lip, tongue, ear lobe or finger) and the thermistor 7 is positioned close to the skin surface.

The window 4 and thermistor 7 are applied in contact with the skin of the subject portion. The thermistor is used in transient mode i.e. current is supplied to the thermistor during the heating period at a rate sufficient to maintain the temperature and therefore resistance of the thermistor at a fixed increment above the initial equilibrium of the thermistor. The resistance of the thermistor is measured by control and processor unit 8. The resistance R can be determined by measuring the current I through and voltage V over the resistor using a current and voltage detector. The resistance R can then be determined as R=V/I. The temperature can then be derived from the temperature–resistance calibration of the thermistor. The current supply source within control and processing unit 8 adjusts the current supplied to the thermistor according to the resistance/temperature value.

The power ($P=I^2R$) supplied to the thermistor is equal to the heat dissipated by the thermistor. The heat dissipated by the thermistor equals the heat flow into the subject so the current supplied (or the power supplied) is a measure of the thermal conductivity of the skin of the subject portion 1.

During the first 2 seconds of the heating period the thermal power dissipated in the thermistor mainly depends on the heat conduction because during this short period of time the capillary network releases very little heat and only in close proximity to the thermistor.

As discussed by G. Delhomme et al, Cardiovascular Mechanics 10, 2081-2082 (1991), the thermal conductivity depends on the water content of the skin according to:

$$K=0.0148 \times \% \text{ water}+1.75 \quad (1)$$

where K: skin thermal conductivity without blood flow in mW/cm° C., water: skin water content in % of skin total weight.

The calculation of the thermal conductivity K during the first two seconds of the heating period makes it possible to determine the skin water content according to equation (1) above.

Control and processor unit 8 determines the water content according to equation (1) above and the power supplied to the thermistor. The determined water content can be used to postpone the detection of the transmitted radiation by detector 6 until the hydration of the skin is within a predetermined range, to reject glucose concentration values determined when the hydration value falls outside a predetermined range or the information can be used to correct for hydration during determination of the glucose concentration.

Control and processor unit 8 may have a pre-defined setting of an acceptable hydration range (e.g. based on the hydration of the skin during a calibration measurement). The control and processor unit 8 will continuously compare the measured hydration value with the pre-defined range until an acceptable hydration value is measured. The glucose concentration value can then be determined by detecting the infrared radiation, emitted by source 2, which is transmitted through subject portion 1. The detector 6 transmits a signal to control and processor unit 8 which determines the glucose concentration from the signal. The measurement is preferably postponed automatically by control and processor unit 8 or may rely on an input from a user.

The optical measurement of glucose concentration may be performed continuously and the control and processing unit 8 may reject the results obtained when the hydration value falls outside the acceptable range.

The hydration level of the skin can be monitored over a predetermined time period by measuring the current or power supplied during the predetermined heating period to maintain a constant temperature.

The skin hydration value may be used to calculate the contribution of water to the transmitted radiation reaching detector 6 and the determination of glucose concentration by control and processor unit 8 can be compensated accordingly. In addition, from the $2^{nd}$ to the $6^{th}$ second of the heating period the thermal power dissipated, and thus the power supplied to the thermistor, depends on both conduction and convection transfer. The difference between the thermal conductivity calculated during the $2^{nd}$ to $6^{th}$ seconds of the heating period and the thermal conductivity calculated during the first 2 seconds of the heating period depends on blood flow. Although FIG. 1 shows a detector for detecting transmitted radiation, reflected radiation could also be detected to determine glucose concentration.

Elements in subsequent figures accorded the same number as an element in FIG. 1 are equivalent to those elements and unless otherwise specified operate in the same manner.

FIG. 2 shows a thermal emission spectroscopy device 14 comprising a detector which detects the thermal emission spectrum 12 originating from subject portion 1. The signal generated by the detector is transmitted to control and processor unit 8 which determines e.g. the glucose concentration from the signal. U.S. Pat. No. 5,666,956 discloses a method and instrument for the non-invasive determination of an analyte (eg glucose) concentration in human body tissue by detecting the infrared radiation naturally emitted by a human body.

The hydration of the skin influences the total amount of radiation that leaves the body so the determination of the skin hydration using the thermistor 7 and processor 8 can be used to improve the accuracy of the analyte (in this example glucose) concentration measurement.

The system of the present invention can also be used with other spectroscopic devices for determining blood analyte concentration, to improve the accuracy of the determined analyte concentration value. Examples of such spectroscopic devices, beyond those specifically illustrated in FIGS. 2 and 3, include a raman spectroscopy device, a diffuse reflection spectroscopy device, a fluorescent spectroscopy device or an optical coherence tomography device.

FIG. 3 shows a system comprising a pulsed superluminescent diode 18 and acoustic sensors 20. Pulsed light 12 at a wavelength chosen to interact with the analyte e.g. glucose, is fired at the subject portion 1. The light is absorbed by the analyte thereby generating microscopic local heating which results in a rapid rise in temperature. The temperature rise generates an pressure wave 22 (for example an ultrasound pressure wave), which is detected by photo-acoustic sensor 20 on the surface of the skin. The magnitude of the pressure is proportional to the thermal expansion coefficient of the skin, which is glucose dependent. The signal 26 generated by the sensor 20 is indicative of the thermal expansion coefficient of the skin of the subject and is transmitted to processor 8 which determines the blood glucose concentration from the signal.

WO 2004/042382 discloses a method and apparatus for non-invasive measurement of living body characteristics by photoacoustics. One major problem with the known photo acoustic method of determination of glucose concentration is its lack of specificity. The acoustic signal is influenced by many factors, with skin water content being a significant influencing factor. Skin hydration influences the intensity of the irradiating beam reaching the blood vessels, less intensity reaches the blood vessels when skin hydration is high, and also influences the acoustic signal generated because skin hydration has an effect on the thermo-elastic properties of the skin. The skin hydration determined by measuring the thermal coefficient of the skin can be used to improve the accuracy of the glucose concentration value determined by the photoacoustic method.

FIG. 4 shows another alternative system comprising a device 30 based on the metabolic heat conformation (MHC) method of glucose concentration determination applied to subject portion 1. The device 30 transmits at least one signal 31 indicative of blood glucose concentration to control and processor unit 8 which determines the blood glucose concentration from the signal.

Known devices based on the MHC method include two thermistors operated in normal mode (i.e. their resistance is measured to determine their temperature). The two thermistors are used to measure skin temperature and blood flow. Non-invasive measurement of glucose by metabolic heat conformation method is discussed by O. K. Cho et al, Clinical Chemistry 50, 1894-1898 (2004). This method relies on the measurement of the oxidative metabolism of glucose, from which the blood glucose concentration can be inferred. Body heat generated by glucose oxidation is based on the subtle balance of capillary glucose and oxygen supply to the cells of a tissue. The MHC method exploits this relationship to estimate blood glucose by measuring the body heat and the oxygen supply. The relationship can be represented in an equation as:

[Glucose concentration]=Function [Heat generated, Bloodflow rate, Hb, HbO$_2$]

where Hb and HbO$_2$ represent the haemoglobin and oxygenated haemoglobin concentrations, respectively.

The MHC device 30 illustrated in FIG. 4 includes one thermistor 7, which is used in transient mode to determine skin hydration and blood flow and is used in normal mode to measure skin temperature. The hydration and blood flow information obtained using the thermistor is used to improve the accuracy of the blood glucose concentration value determined because the MHC method is based on blood flow and, among other things, thermal conductivity of the skin, diffuse reflectance of the skin and body heat radiated from the skin, all of which are influenced by the level of skin hydration.

FIG. 5 shows a further embodiment of the invention having the same features as shown in FIG. 1 and further including a skin hydrator 9 which moisturises the skin, by e.g. application of water or other hydrating agent, and a skin hydration controller 10. Information from the thermistor 7 is transmitted to the skin hydration controller 10 which is connected in a control loop to skin hydrating device 9 so the hydration of the skin, where the device is positioned and the glucose concentration measurement is being made, can be maintained at a predetermined level and eliminate skin hydration variations affecting the glucose concentration determination. The skin hydration controller 10 and control and processor unit 8 may be comprised in a single item of hardware.

Although the embodiments above have been described with reference to determining the concentration of glucose in a live subject the present invention can also be used in the measurement of other blood analytes or substances in the skin e.g. cholesterol, albumin, lactate or vitamins for which skin hydration is an interferent.

It should be noted that the above-mentioned embodiments illustrate rather than limit the invention, and that those skilled in the art will be capable of designing many alternative embodiments without departing from the scope of the invention as defined by the appended claims. In the claims, any reference signs placed in parentheses shall not be construed as limiting the claims. The word "comprising" and "comprises", and the like, does not exclude the presence of elements or steps other than those listed in any claim or the specification as a whole. The singular reference of an element does not exclude the plural reference of such elements and vice-versa. The invention may be implemented by means of hardware comprising several distinct elements, and by means of a suitably programmed computer. In a system claim enumerating several means, apparatus, devices etc several of these means, apparatus, devices etc may be embodied by one and the same item of hardware. The mere fact that certain measures are recited in mutually different dependent claims does not indicate that a combination of these measures cannot be used to advantage.

The invention claimed is:

1. A non-invasive system for measuring hydration of at least one of a skin and exterior mucosa and detecting a blood analyte concentration of a subject comprising:
   a thermal conductivity measuring apparatus for obtaining a measurement of a thermal conductivity of the at least one of the skin and the exterior mucosa of the subject; and
   a processor configured to determine a hydration value from the thermal conductivity measurement and to determine the blood analyte concentration, wherein the processor is further configured to postpone determination of the blood analyte concentration until the hydration value is within a predetermined range,
   further comprising a hydrating device for providing a hydrating agent to the least one of the skin and the exterior mucosa and a hydration controller connected to the hydrating device so the hydration controller maintains the hydration value at a predetermined level within the predetermined range.

2. The non-invasive system according to claim 1, wherein the thermal conductivity measuring apparatus comprises:
   a thermistor in thermal connection with the at least one of a skin and exterior mucosa of the subject in use: and
   a current supply for supplying current to the thermistor sufficient to maintain the resistance or temperature of the thermistor at a predetermined level,
   wherein the thermal conductivity measuring apparatus obtains a measurement of the thermal conductivity in dependence upon the current supplied to the thermistor.

3. The non-invasive system according to claim 1, wherein the system for detecting the analyte blood concentration comprises one or more of:
- a spectroscopic device;
- a photoacoustic device; and
- a device for determining blood glucose concentration based on the metabolic heat conformation method.

4. The non-invasive system according to claim 1, wherein the analyte concentration is glucose concentration.

5. The non-invasive system of claim 1, wherein the processor is further configured to continuously compare the determined hydration value with the predefined range until the determined hydration value is within the predefined range.

6. The non-invasive system of claim 1, wherein the processor is further configured to determine the blood analyte concentration from a radiation detected by a detector, wherein the radiation is emitted by a source and transmitted through a portion of the subject.

7. The non-invasive system of claim 1, wherein the processor is further configured to determine the blood analyte concentration from a pressure wave detected by an acoustic sensor in response to a pulsed radiation emitted by source to cause a temperature rise that generates the pressure wave.

8. A method for measuring hydration of at least one of a skin and exterior mucosa and a blood analyte concentration of a subject, the method comprising the acts of:
- non-invasively measuring a thermal conductivity of the at least one of the skin and the exterior mucosa;
- determining a hydration level of the at least one of the skin and the exterior mucosa from the thermal conductivity;
- monitoring the hydration level until the hydration level is within a predetermined range;
- when the hydration level is within the predetermined range, determining by a processor the blood analyte concentration; and
- maintaining the hydration level within a predetermined range using a hydration controller for controlling a hydrator for providing a hydrating agent to the least one of the skin and the exterior mucosa.

9. The method of claim 8, wherein the monitoring act includes continuously comparing the determined hydration level with the predefined range until the determined hydration value is within the predefined range.

10. The method of claim 8, wherein the act of determining the blood analyte concentration is performed using a radiation detected by a detector, wherein the radiation is emitted by a source and transmitted through a portion of the subject.

11. The method of claim 8, wherein the act of determining the blood analyte concentration is performed using a pressure wave detected by an acoustic sensor in response to a pulsed radiation emitted by source to cause a temperature rise that generates the pressure wave.

12. The method of claim 8, wherein the analyte concentration is glucose concentration.

* * * * *